United States Patent [19]

Umezawa et al.

[11] Patent Number: 4,474,946
[45] Date of Patent: Oct. 2, 1984

[54] DI-N$^{6'}$, O$^3$-DEMETHYLISTAMYCIN A PREPARATION

[75] Inventors: Hamao Umezawa, Tokyo; Shinichi Kondo, Yokohama; Daishiro Ikeda, Tokyo, all of Japan

[73] Assignee: Zaidan Hojin Biseibutsu Kagaku Kenkyu Kai, Tokyo, Japan

[21] Appl. No.: 530,006

[22] Filed: Sep. 7, 1983

Related U.S. Application Data

[62] Division of Ser. No. 241,649, Mar. 9, 1981, Pat. No. 4,379,687.

[30] Foreign Application Priority Data

Mar. 28, 1980 [JP] Japan .................................. 55-38889

[51] Int. Cl.$^3$ ............................................. C07H 15/22
[52] U.S. Cl. ................... 536/16.8; 536/124; 536/16.1
[58] Field of Search ...................... 536/16.8, 16.1, 124

[56] References Cited

U.S. PATENT DOCUMENTS

| | | | |
|---|---|---|---|
| 4,231,924 | 11/1980 | Tadanier et al. | 536/16.1 |
| 4,251,516 | 2/1981 | Martin et al. | 536/16.1 |
| 4,282,211 | 8/1981 | McAlpine et al. | 536/16.1 |
| 4,330,673 | 5/1982 | Rosenbrook, Jr. | 536/16.1 |
| 4,362,866 | 12/1982 | Igarashi et al. | 536/16.8 |
| 4,370,475 | 1/1983 | Igarashi et al. | 536/16.8 |
| 4,382,926 | 5/1983 | Umezawa et al. | 536/16.1 |
| 4,406,891 | 9/1983 | Umezawa et al. | 536/16.8 |

Primary Examiner—Johnnie R. Brown
Attorney, Agent, or Firm—Larson and Taylor

[57] ABSTRACT

A new istamycin A derivative called di-N$^{6'}$, O$^3$-demethylistamycin A exhibits a high antibacterial activity against various bacteria, particularly *Pseudomonas aeruginosa*. This compound can be prepared by selective acylation of the methylamino group at the 4-position of 1,2',6'-tri-N-protected N$^4$-deglycyl-di-N$^{6'}$, O$^3$-demethylistamycin A with glycine or an N-protected derivative thereof, followed by N-deprotection.

1 Claim, No Drawings

DI-N⁶′, O³-DEMETHYLISTAMYCIN A PREPARATION

This is a division of application Ser. No. 241,649 filed Mar. 9, 1981, now U.S. Pat. No. 4,379,687.

SUMMARY OF THE INVENTION

This invention relates to a new derivative of istamycin A denoted as di-$N^{6'}$,$O^3$-demethylistamycin A, (that is 6′-N,3-O-didemethylistamycin A) which is a synthetic aminoglycosidic antibiotic useful as antibacterial agent, to a process for the preparation thereof and also to therapeutical uses of the new derivative.

BACKGROUND OF THE INVENTION

We described and claimed new, useful antibiotics called istamycin A and istamycin B which are produced by cultivation of a new species of Streptomyces, namely Streptomyces tenjimariensis SS-939 strain (FERM-P 4932 or ATCC 31603) and which are highly active against a wide variety of gram-negative and gram-positive bacteria (see the "Journal of Antibiotics" 32, 964–966 (September, 1979); U.K. patent application No. GB 2048855A published Dec. 17, 1980). We have made extensive studies on the synthetic production of istamycin A starting from 3′,4′-dideoxyneamine (see "Journal of Antibiotics" 32, 1365–1366 (1979)). In a further development of our extensive studies, we have now successfully prepared a new derivative of istamycin A, di-$N^{6'}$,$O^3$-demethylistamycin A in a facile way, and we have found that di-$N^{6'}$,$O^3$-demethyistamycin A exhibits a high antibacterial activity against a wide range of gram-negative and gram-positive bacteria and particularly be more active against Pseudomonas aeruginosa than istamycin An object of this invention is to provide a new antibiotic derivative of istamycin A which is useful as antibacterial agent for therapeutic treatment of bacterial diseases in man and animals and also for sterilization of surgical materials and instruments. Another object of the invention is to provide a process for the synthesis of said new antibiotic derivative of istamycin A. Further object of the invention is to provide a pharmaceutical composition comprising the new antibiotic derivative of istamycin A as active ingredient.

Other objects and advantages will be apparent from the following descriptions.

DETAILED DESCRIPTION OF THE INVENTION

According to a first aspect of this invention, there are provided, as new antibiotic substances, di-$N^{6'}$,$O^3$-demethylistamycin A of the structural formula (I):

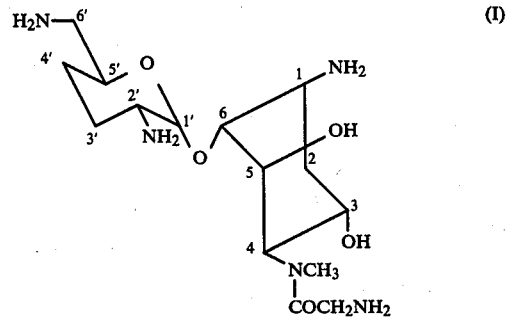

and acid addition salts thereof.

Istamycin A has the following structural formula:

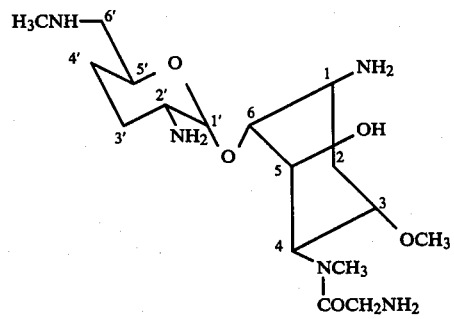

Thus, the compound of formula (I) is corresponding to one derivative of istamycin A from which the two methyl groups of the methoxy group at 3-position and of the methylamino group at 6′-position have been eliminated.

The new compound (I) of this invention has the physico-chemical and biological properties as follows:

Monocarbonate of di-$N^{6'}$,$O^3$-demethylistamycin A is in the form of colorless powder which has no definite melting point, decomposes at 138°–145° C., gives a specific optical rotation of $[\alpha]_D^{22}$ +136° (c 0.36 in water) and indicates an elemental analysis: Found: C, 45.39; H, 7.63; N, 16.42% which is consistent with the theoretical values of $C_{15}H_{31}N_5O_5 \cdot H_2CO_3$(C, 45.38; H, 7.85; N, 16.54%). Mass spectrometry of the monocarbonate shows the peak of (M+1)⁺ at m/e=362 and thin layer chromatography thereof on silica gel gives a single spot (positive to ninhydrin reagent) at $R_f$ 0.06 when developed with the lower phase of a mixed solvent of chloroform-methanol-28% aqueous ammonia (2:1:1 by volume) or at $R_f$ 0.46 when developed with a mixed solvent of butanol-ethanol-chloroform-17% aqueous ammonia (4:5:2:5 by volume).

The compound of above formula (I) exhibits a high antibacterial activity against a wide variety of gram-negative and gram-positive bacteria as is clear from the antibacterial spectra set out in Table 1 below where those of istamycin A are also shown by way of comparison. The minimum inhibitory concentrations (mcg/ml) indicated have been determined according to a standard serial dilution method on nutrient agar plates which were incubated at a temperature of 37° C. for 17 hours. The results of Table 1 reveal that the di-demethylistamycin A of this invention is substantially more active particularly against Pseudomonas aeruginosa than istamycin A.

TABLE 1

| Test Microorganisms | Minimum Inhibitory Concentrations (mcg/ml) | |
| --- | --- | --- |
| | Di-demethyl-istamycin A | Istamycin A |
| *Staphylococcus aureus* FDA 209P | 1.56 | 0.78 |
| *Staphylococcus aureus* Smith | <0.20 | <0.20 |
| *Staphylococcus aureus* Ap 01 | 1.56 | 0.78 |
| *Staphylococcus epidermidis* 109 | 1.56 | 0.78 |
| *Micrococcus flavus* FDA 16 | 3.13 | 3.13 |
| *Sarcina lutea* PCI 1001 | 0.78 | 0.20 |
| *Bacillus anthracis* | 0.39 | <0.20 |
| *Bacillus subtilis* PCI 219 | <0.20 | <0.20 |
| *Bacillus subtilis* NRRL B-558 | <0.20 | 0.39 |
| *Bacillus cereus* ATCC 10702 | 3.13 | 3.13 |
| *Corynebacterium bovis* 1810 | 1.56 | 1.56 |
| *Mycobacterium smegmatis* ATCC 607 | 0.39 | 1.56 |
| *Escherichia coli* NIHJ | 6.25 | 3.13 |
| *Escherichia coli* K-12 | 6.25 | 1.56 |
| *Escherichia coli* K-12 R5 | 100 | 3.13 |
| *Escherichia coli* K-12 R388 | 1.56 | 0.78 |
| *Escherichia coli* K-12 J5R11-2 | 3.13 | 3.13 |
| *Escherichia coli* K-12 ML1629 | 3.13 | 3.13 |
| *Escherichia coli* K-12 ML1630 | 12.5 | 3.13 |
| *Escherichia coli* K-12 ML1410 | 6.25 | 3.13 |
| *Escherichia coli* K-12 ML1410 R81 | 3.13 | 1.56 |
| *Escherichia coli* K-12 LA290 R55 | 12.5 | 3.13 |
| *Escherichia coli* K-12 LA290 R56 | 3.13 | 1.56 |
| *Escherichia coli* K-12 LA290 R64 | 3.13 | 1.56 |
| *Escherichia coli* W677 | 3.13 | 1.56 |
| *Escherichia coli* JR66/W677 | 6.25 | 3.13 |
| *Escherichia coli* K-12 C600 R135 | >100 | >100 |
| *Escherichia coli* JR225 | 3.13 | 1.56 |
| *Klebsiella pneumoniae* PCI602 | 3.13 | 1.56 |
| *Klebsiella pneumoniae* 22#3038 | 12.5 | 3.13 |
| *Shigella dysenteriae* JS11910 | 12.5 | 3.13 |
| *Shigella flexneri* 4B JS11811 | 12.5 | 6.25 |
| *Shigella sonnei* JS11756 | 6.25 | 6.25 |
| *Salmonella typhi* T-63 | 3.13 | 0.78 |
| *Salmonella enteritidis* 1891 | 6.25 | 3.13 |
| *Proteus vulgaris* OX19 | 1.56 | 0.78 |
| *Proteus rettgeri* GN311 | 50 | 25 |
| *Proteus rettgeri* GN466 | 12.5 | 6.25 |
| *Serratia marcescens* | 12.5 | 6.25 |
| *Serratia* sp. SOU | >100 | >100 |
| *Serratia* sp. 4 | 50 | 50 |
| *Providencia* sp. Pv16 | 12.5 | 6.25 |
| *Providencia* sp. 2991 | 12.5 | 25 |
| *Pseudomonas aeruginosa* A3 | 3.13 | 6.25 |
| *Pseudomonas aeruginosa* No. 12 | 25 | 100 |
| *Pseudomonas aeruginosa* H9 | 12.5 | 25 |
| *Pseudomonas aeruginosa* H11 | 50 | 100 |
| *Pseudomonas aeruginosa* TI-13 | 12.5 | 25 |
| *Pseudomonas aeruginosa* GN 315 | 25 | 25 |
| *Pseudomonas aeruginosa* 99 | >100 | >100 |
| *Pseudomonas aeruginosa* B-13 | >100 | >100 |
| *Pseudomonas aeruginosa* 21-75 | >100 | >100 |
| *Pseudomonas aeruginosa* PST 1 | 50 | 100 |
| *Pseudomonas aeruginosa* ROS 134/PV 21 | 50 | 100 |
| *Pseudomonas aeruginosa* K-Ps 102 | 12.5 | 50 |
| *Pseudomonas maltophilia* GN 907 | >100 | >100 |

The compound of this invention, di-N$^6$',O$^3$-demethylistamycin A is usually obtained in the form of free base or its hydrate or carbonate, which can be converted into the form of any pharmaceutically acceptable non-toxic acid addition salt by reaction with a pharmaceutically acceptable acid in a conventional manner. Examples of the pharmaceutically acceptable acid to be used for this purpose include inorganic acids such as hydrochloric, hydrobromic, sulfuric, phosphoric and nitric acids and organic acids such as acetic, malic, citric, ascorbic and methanesulfonic acids.

According to a second aspect of this invention, there is provided a process for preparing the compound of above formula (I), which comprises concurrently blocking with an amino-protecting group the three amino groups at the 1-, 2'- and 6'-positions of the compound of the structural formula (VIII):

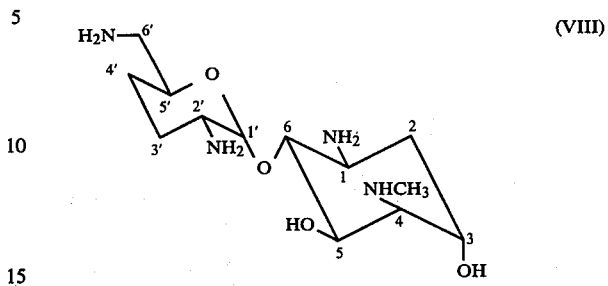

reacting the resultant tri-N-protected derivative of the compound (VIII) with glycine or an N-protected glycine whose the amino group has been blocked with an amino-protecting group or with a functional equivalent of said glycine to acylate the unprotected methylamino group at the 4-position of the compound (VIII), and removing all the remaining amino-protecting groups from the acylation product. The process of this invention may include further a step of converting the compound (I) thus produced into its acid addition salt or converting an acid addition salt of the compound produced into the free base or another acid addition salt thereof by a conventional method.

The starting compound of formula (VIII) to be used in the present process, which is denoted as N$^4$-deglycyl-di-N$^6$',O$^3$-demethylistamycin A, may be prepared using as initial material 3',4'-dideoxyneamine which, in turn, can be made by a known technique as described in "Journal of Antibiotics" 24, 711–712 (1971) or "Bulletin of the Chemical Society of Japan" 46, 3507–3510 (1973).

The method of preparing the initial compound (VIII) is summarized as follows: The four amino groups existing in 3',4'-dideoxyneamine of the formula (II):

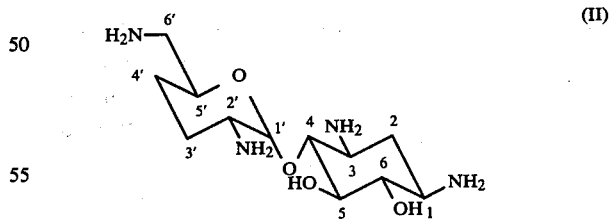

are blocked with an amino-protecting group of urethane-forming type and then converted into the 1,6-cyclic carbamate derivative of the N-protected compound (II) by treating with a base such as an alkali metal hydride. The hydroxyl group at 5-position of the 1,6-cyclic carbamate derivative is blocked with a hydroxyl-protecting group to produce a compound of the formula (III):

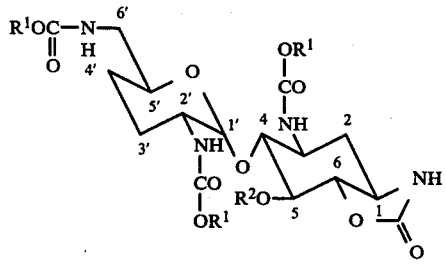

(III)

wherein each R¹OCO—represents the monovalent amino-protecting group of urethane-forming type where R¹ is an alkyl group (eg. alkyl of 1–6 carbon atoms), cycloalkyl group (eg. cycloalkyl of 5–6 carbon atoms) or aralkyl group (eg. phenyl-$C_{1-4}$ alkyl such as benzyl) and R² represents an alkyl group (eg. alkyl of 1–6 carbon atoms), benzyl group or tetrahydropyranyl group as the hydroxyl-protecting group. Subsequently, the compound of formula (III) is treated with an alkali such as aqueous sodium or barium hydroxide to hydrolyze the 1,6-cyclic carbamate ring, followed by protection of the resultant free amino group at the 1-position with an amino-protecting group of urethane-forming type different from the aforesaid amino-protecting group R¹OCO—, and by sulfonylation of the resultant free hydroxyl group at the 6-position with a sulfonylation reagent of the formula $R^4SO_3H$ or a reactive equivalent thereof to produce a compound of the formula (IV):

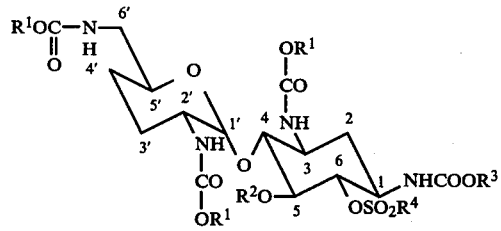

(IV)

wherein R¹ and R² have the same meanings as above, R³OCO—represents the monovalent amino-protecting group of urethane-forming type where R³ is an alkyl group (eg. alkyl of 1–6 carbon atoms), cycloalkyl group (eg. cycloalkyl of 5–6 carbon atoms) or aralkyl group (eg. benzyl) but different from the group R¹, and R⁴ represents an alkyl (eg. alkyl of 1–4 carbon atoms), aryl (eg. phenyl or methylphenyl) or aralkyl (eg. benzyl) group. The compound of formula (IV) is then treated with a base such as alkali metal alcoholate to form a compound bearing an aziridine ring and having the formula (V):

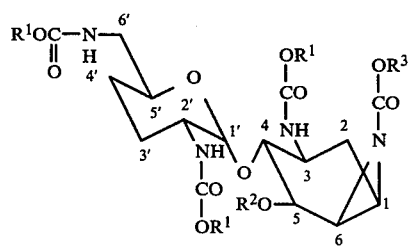

(V)

wherein R¹, R² and R³ are as defined above. The compound of formula (V) is further treated with an alkali metal salt of an organic acid such as a lower alkanoic acid or benzoic acid to open the aziridine ring, thereby to produce a compound of the formula (VI):

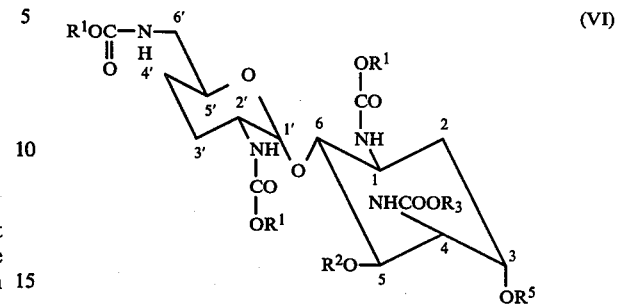

(VI)

wherein R¹, R² and R³ are as defined above and R⁵ represents an acyl group such as alkanoyl or benzoyl group which originates from the organic acid employed. The hydroxyl-protecting groups (R² and R⁵) at the 3- and 5-positions of the compound (VI) are removed from the latter in a conventional way. If necessary (that is, where the 4-amino-protecting group —COOR³ has eventually been removed during the treatment with the organic acid alkali metal salt or concurrently with the removal of the hydroxyl-protecting groups R², R⁵), further amino-protecting (—COOR³) of urethane-forming type is newly introduced into the free 4-amino group to give a compound of the formula (VII):

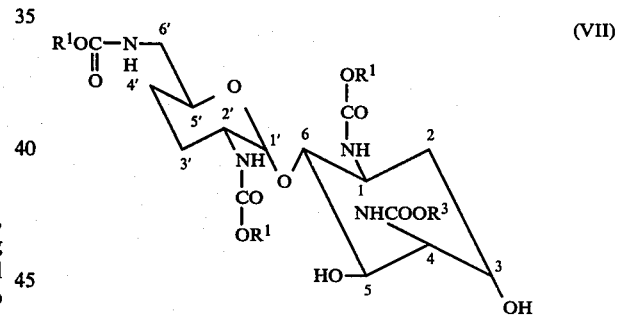

(VII)

in which R¹ and R³ are as defined above. Thereafter, the amino-protecting groups (—COOR¹) at the 1-, 2'- and 6'-positions of the compound (VII) are removed therefrom in a usual manner but with retaining the 4-amino-protecting group (—COOR₃) deprotected, followed by reduction with a metal hydride to convert the protected 4-amino group (—NHCOOR³) into the 4-methylamino group. There is thus produced the compound of above formula (VIII).

The following describes a favorable embodiment of the method for the preparation of the starting compound (VIII).

In the first step, the four amino groups at the 1-, 3-, 2'- and 6'-positions of 3',4'-dideoxyneamine of above formula (II) are blocked with a known amino-protecting group of urethane-forming type to give an N-protected derivative of 3',4'-dideoxyneamine having the formula (II'):

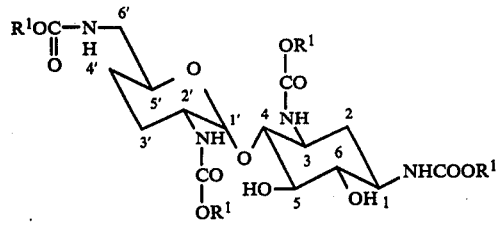

(II′)

in which each R$^1$OCO— stands for the monovalent amino-protecting group of urethane-forming type where R$^1$ is an alkyl, cycloalkyl or aralkyl group as described hereinbefore. The amino-protecting group to be used for this purpose is one capable of reacting the adjacent hydroxyl group (where exists) to form a cyclic carbamate ring when treated with a base in the subsequent step. Examples of the amino-protecting group available for this purpose include alkyoxycarbonyl groups of 2–7 carbon atoms such as tert-butoxycarbonyl and tert-amyloxycarbonyl; cycloalkyloxycarbonyl groups of 6–7 carbon atoms such as cyclohexyloxycarbonyl and aralkyloxycarbonyl groups such as benzyloxycarbonyl and para-methoxybenzyloxycarbonyl. Among these it is preferred to use an amino-protecting group of urethane-forming type which is readily removable without cleaving the amino-protecting group —COOR$_3$ which will have been introduced later into the 1-amino group of the compound of formula (IV). To this end, it is thus recommendable to select an aralkyloxycarbonyl group which can be removed by hydrogenolysis. The introduction of the amino-protecting group —OCOR$_1$ may easily be accomplished by any conventional procedure, for example, by reaction with a known amino-protecting reagent in the form of acid halide, acid azide or active ester.

In the second step, the compound of formula (II′) is treated with a base such as metal hydride to give a compound in the form of the 1,6-cyclic carbamate having the formula (II″):

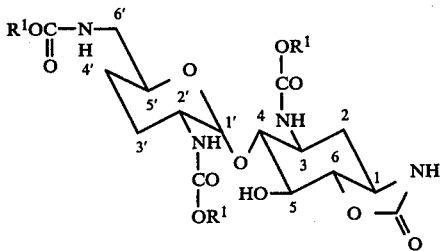

(II″)

wherein R$^1$ is as defined above. Amongst the four amino-protecting groups of the N-protected compound (II′), the amino-protecting group at the 1-position is readily reacted even at a low temperature, for example, below 0° C. with the adjacent hydroxyl group at the 6-position to form the cyclic carbamate when it is treated with a base such as an alkali metal hydride, eg. sodium hydride or lithium hydride in an appropriate organic solvent such as anhydrous dimethylformamide.

In the third step, the hydroxyl group at the 5-position of the cyclic carbamate compound (II″) is blocked with a known hydroxyl-protecting group in a usual way to produce a compound of formula (III) indicated hereinbefore. This step is followed by treatment with an aqueous alkali to hydrolyze the 1,6-cyclic carbamate ring, affording a compound of the formula (III′):

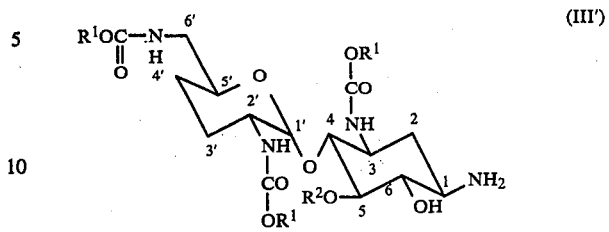

(III′)

The protecting group (R$^2$) for blocking the 5-hydroxyl group of the compound (II″) must be insusceptible to the conditions under which said alkaline hydrolysis of the 1,6-cyclic carbamate compound (III) be conducted. Thus, amongst known hydroxyl-protecting groups are selected those of ether-type such as alkyl ethers and benzyl ethers and those of acetal-type such as tetrahydropyranyl, all of which can be introduced into the 5-hydroxyl group by any conventional hydroxyl-protecting technique. In particular, for the hydroxyl-protecting group R$^2$, it is preferred to use tetrahydropyranyl group which is readily removable by hydrolysis under mild acidic conditions.

The subsequent hydrolysis of the 1,6-cyclic carbamate compound (III) can be achieved by treating in a dilute aqueous solution of an alkali or alkaline earth metal hydroxide such as sodium hydroxide or barium hydroxide and leads to opening of the 1,6-cyclic carbamate ring into the form of a free aminoalcohol represented by above formula (III′). The hydrolysis may preferably be carried out at an elevated temperature of 40° to 60° C. and at an alkali concentration of 0.1M or less. These reaction conditions will not bring about removal of the other amino- and hydroxyl-protecting groups and so give rise to preferential formation of the 1,6-aminoalcohol compound of formula (III′).

Further, the 1-amino group so liberated of the compound (III′) is blocked with an amino-protecting group (—COOR$_3$) of urethane-forming type which is different from the group R$^1$OCO— existing to block the amino groups of the compound (II), and the 6-hydroxyl group is sulfonylated by reaction with a sulfonylating reagent, for example, a sulfonyl halide of the formula: R$^4$SO$_2$X in which R$^4$ is the alkyl, aryl or aralkyl group and X is chlorine or bromine atom. There is thereby produced a compound of above formula (IV).

As the urethane-forming type group of protecting the 1-amino group of the compound (III′), it is particularly preferred to use an alkyoxycarbonyl group since the latter can be selectively retained in the compound to be produced upon the later treatment for removal of the other amino-protecting groups at the 3-, 2′- and 6′-positions and is advantageous for the reductive formation of methylamino group at the 4-position of the compound (VII) as stated later.

The above-mentioned sulfonylation of the 6-hydroxyl group may be smoothly effected, at ambient temperature in a good yield by reacting in a suitable organic solvent such as dry pyridine with a known sulfonylation reagent such as sulfonyl halide of the formula R$^4$SO$_2$X, especially methanesulfonyl, para-toluenesulfonyl or benzylsulfonyl chloride.

In the next step, the compound of formula (IV) is treated with a base to form a compound of above formula (V) carrying the aziridine ring, followed by further treatment with an alkali metal salt of an organic acid to open the aziridine ring.

The aziridine compound (V) may be obtained in a good yield by treating the compound (IV) with a base such as an alkali metal alcoholate for example, sodium alcoholate, especially sodium methylate in an anhydrous organic solvent such as dry tetrahydrofuran. The reaction to form the aziridine ring may proceed even at a low temperature of 0° to 10° C., at which the reaction will be genrally completed in 24 hours.

The aziridine compound (V) thus produced, which is an important new intermediate for the preparation of the object compound according to this invention, may be directly (i.e. without purification) subjected to the subsequent ring-opening reaction.

The opening of the aziridine ring in the compound (V) may be effected with a favorable yield by reacting with an alkali metal salt of an organic acid such as a lower alkanoic acid or benzoic acid and especially with for example, sodium benzoate or sodium acetate in an anhydrous organic solvent such as dry dimethylformamide. The reaction gives a further form of aminocyclitol having the formula (VI):

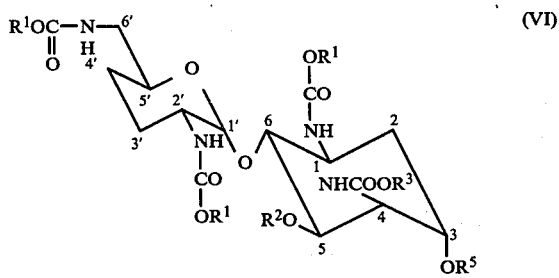
(VI)

wherein $R^1$, $R^2$ and $R^3$ are as defined hereinbefore and $R^5$ is the acyl group such as alkanoyl or benzoyl group which originates from the organic acid employed.

As will be seen from formulae (IV) and (VI), exchange takes place between the position of the amino group and the position of the hydroxyl group upon the opening of the aziridine ring, when generally the urethane-type protecting group is remaining in the amino group while the acyl group originating from the organic acid used in the ring-opening reaction is introduced into the hydroxyl group as shown by above formula (VI). With respect to the new form of aminocyclitol (1,4-diamino-1,2,4-trideoxyaminocyclitol derivative) of formula (VI), the numbering of the aminocyclitol moiety is given based upon that of fortimicin and istamycin. The same numbering applies to formulae (VII), (VII') and (VIII). As regards the aminocyclitol compounds (1,3-diamino-1,2,3-trideoxy-aminocyclitol derivatives) represented by above formulae (I)–(V), the numbering is given based on that of 2-deoxystreptamine.

The hydroxyl-protecting groups ($R^2$ and $R^5$) at the 3- and 5-positions of the compound (VI) are then removed from the latter to produce the compound of formula (VII) indicated hereinbefore. The acyl group ($R^5$) as the hydroxyl-protecting group at the 3-position can readily be removed by alkaline hydrolysis with a common base, for instance, methanolic ammonia solution, while the hydroxyl-protecting group ($R^2$) at the 5-position such as tetrahydropyranyl group be removed by acidic hydrolysis under mild acidic conditions as already stated, for example, by treatment with an aqueous solution of trifluoroacetic acid at a low temperature of 0° to 10° C.

In some cases, the amino-protecting group (—$COOR_3$) at the 4-position may be cleaved in the course of the aforesaid reaction for opening of the aziridine ring or sometime concurrently with the removal of the hydroxyl-protecting groups ($R^2$, $R^5$). It is then necessary that the amino-protecting group of urethane-forming type which is different from that (—$OCOR^1$) used to block the 1-, 2'- and 6'-amino groups should be re-introduced into the free 4-amino group. This is, for example, the case where the amino-protecting group at the 4-position is tert-butoxycarbonyl group which can be cleaved simultaneously with the removal of the hydroxyl-protecting group ($R^2$) at the 5-position by mild acidic hydrolysis. The amino-protecting group (—$COOR_3$) of urethane-forming type to be re-introduced into the 4-amino group in such case should desirably be insusceptible to the subsequent reaction for removal of the other amino-protecting groups (—$OCOR_1$) at the 1-, 2'- and 6'-positions and should be available for the formation of the methylamino group at the 4-position. Preferred examples thereof are methoxycarbonyl and ethoxycarbonyl groups.

Sebsequently, the amino-protecting group (—$OCOR^1$) at the 1-, 2'- and 6'-positions of the compound (VII) are selectively removed therefrom by a conventional deprotecting technique which is known for removal of the protective groups —$OCOR^1$ but is not effective to remove the protective group —$COOR^3$ at the 4-position, whereby there is produced a 4-N-protected $N^4$-deglycyl-tri-$N^4$,$N^{6'}$,$O^3$-demethylistamycin A of the formula (VII'):

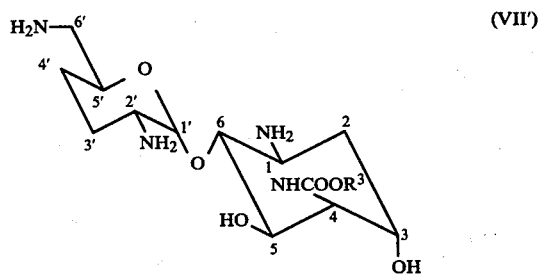
(VII')

in which $R^3$ is as defined above.

In the final step, the compound (VII') is reduced with a metal hydride so that the protected 4-amino group (—$NHCOOR^3$) is converted into the 4-methylamino group (ie. 4-N-methylation), affording $N^4$-deglycyl-di-$N^{6'}$,$O^3$-demethylistamycin A of the formula (VIII):

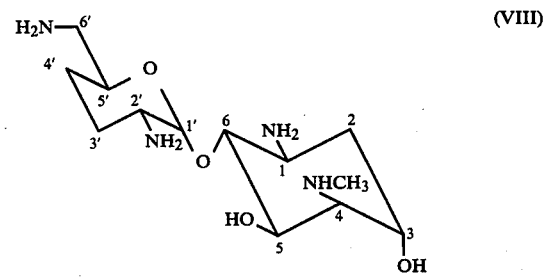
(VIII)

The 4-N-methylation may be carried out by reducing the compound (VII') with a metal hydride such as lithium aluminium hydride or boron hidride in an anhydrous organic solvent such as dry tetrahydrofuran. The reaction is generally effected at a temperature of 40° to 60° C. for a period of 10 hours or longer.

The compound $N^4$-deglycyl-di-$N^{6'},O^3$-demethylistamycin A thus produced, which is used as the starting material in the process of this invention, has the following properties:

Monocarbonate of $N^4$-deglycyl-di-$N^{6'},O^3$-demethylistamycin A is in the form of colorless powder which has no definite melting point, decomposes at 115°–118° C., gives a specific optical rotation of $[\alpha]_D^{22}$ +102° (c 0.65, water) and indicates an elemental analysis: Found: C, 46.15; H, 7.97; N, 15.37% which is coincident with the theoretical values of $C_{13}H_{25}N_4O_4 \cdot H_2CO_3$ (C, 45.89; H, 8.25; N, 15.29%). Mass spectrometry of the monocarbonate shows the M+ peak at m/e=304, and thin layer chromatography thereof on silica gel gives a single spot (positive to ninhydrin reagent) at $R_f$ 0.12 when developed with the lower phase of a mixed solvent of chloroform-methanol-28% aqueous ammonia (2:1:1 by volume) or at $R_f$ 0.50 when developed with a mixed solvent of butanol-ethanol-chloroform-17% aqueous ammonia (4:5:2:5 by volume).

According to the process of the invention, principally the object compound of this invention, di-$N^{6'},O^3$-demethylistamycin A of formula (I) is prepared by acylation with glycine (namely glycylation) of the methylamino group at the 4-position of the compound (VIII). In order to make selective glycylation of the 4-methylamino group in a high yield, it is necessary to block previously the other amino groups at the 1-, 2'- and 6'-positions with an amino-protecting group. Fortunately, there is a considerable difference in reactivity between these three amino groups and the 4-methylamino group. Thus, an N-protected derivative of the compound (VIII) whose three amino groups at the 1-, 2'- and 6'-positions have been blocked can be prepared with a high yield by a conventional method for introduction of a known amino-protecting group, for example, by reacting the compound (VIII) with 3–3.5 molar equivalents of a known amino-protecting reagent in the form of acid halide, acid azide, active ester or acid anhydride. Examples of the known amino-protecting group for this purpose include alkoxycarbonyl groups such as tert-butoxycarbonyl and tert-amyloxycarbonyl; cycloalkyloxycarbonyl groups such as cyclohexyloxycarbonyl; aralkyloxycarbonyl groups such as benzyloxycarbonyl; acyl groups such as trifluoroacetyl and O-nitrophenoxyacetyl; phosphinothioyl groups such as diphenylphosphinothioyl and dimethylphosphinothioyl; and phosphinyl groups such as diphenylphosphinyl. Known divalent amino-protecting groups may be used to block the amino groups into the form of Schiff base, too.

The 1,2',6'-tri-N-protected derivative of $N^4$-deglycyl-di-$N^{6'},O^3$-demethylistamycin A so prepared may be directly used without purification, for the subsequent glycylation of the 4-methylamino group. The 4-N-glycylation reaction may be carried out using glycine itself or a functional equivalent thereof according to any known technique employed for synthesis of peptides. The functional equivalent of glycine for present use includes dicyclohexylcarbodiimides, mixed acid anhydrides, azides and active esters of glycine. It is preferred that the amino group of glycine should be previously blocked with an amino-protecting group which may be the same as or different from that used for the amino groups of the compound (VIII). Preferred examples of the amino-protecting group to be conveniently used are the benzyloxycarbonyl group which is removable by hydrogenolysis in the presence of a catalyst such as palladium or platinum oxide or the tert-butoxycarbonyl group which is removable by acidic hydrolysis, for example, in aqueous trifluoroacetic or acetic acid solution or dilute hydrochloric acid solution.

In a preferred embodiment of the present process, the 4-N-glycylation reaction can be performed using an active ester of an N-protected glycine at an elevated temperature of 40°–60° C. in a suitable organic solvent such as dioxane. As the active ester of high reactivity, there may be mentioned N-hydroxysuccin-imide ester of N-benzyloxycarbonylglycine which may be made in a conventional way and which can be used for the glycylation in a proportion of 1 to 1.5 molar equivalents.

After the completion of the glycylation, all the amino-protecting groups remaining in the reaction product are removed by a conventional method, for example, by hydrogenolysis or acidic hydrolysis as stated hereinabove, whereby there is produced the object compound of formula (I).

As already described, the new compound (I) of this invention possesses a high antibacterial activity against a wide variety of bacteria. Further, the compound has a low toxicity to animals as shown by the results that mice tolerated intravenous administration of 100 mg/Kg of the compound. Thus, the compound is very useful as an antibacterial agent and for this purpose it is generally formulated into the form of pharmaceutical composition, which may be administered into man or an animal in a way known per se.

Accordingly, this invention also provides a pharmaceutical composition comprising a therapeutically or bactericidally effective amount of the compound of above formula (I) or a pharmaceutically acceptable acid addition salt thereof in combination with a pharmaceutically acceptable carrier or adjuvant. This invention further provides a mehtod of inhibiting the bacterial growth in an animal which comprises administering a therapeutically or bactericidally effective amount of the compound (I) or a pharmaceutically acceptable salt thereof to an animal infected with or susceptible to bacteria. It will be appreciated that an appropriate amount of the effective ingredient to be administered for the envisaged purpose will vary depending upon the particular composition formulated, the mode of administration, the conditions to be treated and the nature of the bacteria to be controlled thereby. By way of general guidance, the effective ingredient will be administered into an animal at a dosage of 0.5–5 mg per kg of the animal body.

This invention is further illustrated but not limited by the following Example.

EXAMPLE 1

Synthesis of di-$N^{6'},O^3$-demethylistamycin A of formula (I)

(a) Preparation of 1,3,2',6'-tetra-N-benzyloxycarbonyl-3',4'-dideoxyneamine ($R^1$=benzyl in formula II')

2.10 g (7.23 mmol) of 3',4'-dideoxyneamine was dissolved in 100 ml of a mixture of water and methanol (1:5 by volume), and to the solution were added 11.9 g (4.3 mmol) of benzyl 4,6-dimethylpyrimidyl-2-thiolcarbonate and 2.3 ml of triethylamine, followed by agitation at ambient temperature for 15 hours. The resultant reaction solution was concentrated to dryness under reduced pressure and the residue was washed successively with 300 ml of water and 200 ml of ethyl ether to give 6.0 g (100%) of the title compound in the form of pale yellow powder. Decomposition point 237°–238° C. $[\alpha]_D^{20}$ +45° (c 2, $CHCl_3$).

(b) Preparation of
3,2',6'-tri-N-benzyloxycarbonyl-3',4'-dideoxyneamine
1,6-carbamate ($R^1$=benzyl in formula II'')

1.34 g (1.62 mmol) of the product obtained in step (a) above was dissolved in 13 ml of anhydrous dimethylformamide, to which was then added 235 mg (4.9 mmol) of sodium hydride (50% suspension in oil) under ice-cooling under an atmosphere of argon gas. The mixture was stirred at room temperature for 4 hours, after which the resulting reaction solution was neutralized with acetic acid and poured into 500 ml of ice-water to separate a precipitate. The precipitate was collected by filtration and purified by column chromatography on silica gel (50 g of Wako-gel C-200 made by Wakojunyaku Co., Japan) developed with mixture solvents of chloroform/acetone (2:1 and 1:1 by volume) to yield 683 mg (62%) of the titled compound. $[\alpha]_D^{28}$ +58° (c 2, $CHCl_3$). $R_f$ 0.25 in thin layer chromatography (TLC) on silica gel developed with chloroform-ethanol (20:1).

(c) Preparation of
3,2',6'-tri-N-benzyloxycarbonyl-3',4'-dideoxy-5-O-tetrahydropyranylneamine 1,6-carbamate ($R^1$=benzyl and $R^2$=tetrahydropyranyl in formula III)

3.7 g (5.15 mmol) of the product obtained in step (b) above was dissolved in 50 ml of dimethylformamide, and to the solution were added 1.3 g (15.5 mmol) of 3,4-dihydro-2H-pyran and 196 mg (1.14 mmol) of anhydrous para-toluenesulfonic acid. The mixture was allowed to stand at ambient temperature for 72 hours, and 1 ml of triethylamine was added to the resultant reaction solution which was then evaporated under reduced pressure to leave a residue. The latter was chromatographed on silica gel (300 g of Wako-gel C-200) using chloroform-ethanol (100:1) as developing solvent to afford 2.4 g (57%) of the title compound. Decomposition point 79°–83° C. $[\alpha]_D^{22}$ +33° (c 0.5, $CHCl_3$). $R_f$ 0.51 in TLC on silica gel developed with chloroform-ethanol (15:1).

(d) Preparation of
3,2',6'-tri-N-benzyloxycarbonyl-1-N-tert-butoxycarbonyl-3',4'-dideoxy-6-O-mesyl-5-O-tetrahydropyranyl-neamine ($R^1$=benzyl, $R^2$=tetrahydropyranyl, $R^3$=tert-butyl and $R^4$=methyl in formula IV)

2.3 g (2.86 mmol) of the product from step (c) above was dissolved in 80 ml of dioxane, and 25 ml of 0.05M barium hydroxide was added to the resulting solution. The mixture was stirred at 60° C. for 30 minutes, followed by further addition of 30 ml of 0.05M barium hydroxide in water and agitation for one hour. Another 30 ml of 0.05M barium hydroxide was then added and the whole mixture was agitated for further one hour to open the 1,6-cyclic carbamate ring. After completion of the reaction, gaseous carbon dioxide was passed into the reaction solution to separate a precipitate, which was filtered off. The filtrate was evaporated under reduced pressure and the residue was extracted with 200 ml of chloroform. The extract was concentrated to dryness under reduced pressure to give 2.24 g of a pale yellow powder of 3,2',6'-tri-N-benzyloxycarbonyl-3',4'-dideoxy-5-O-tetrahydropyranylneamine ($R^1$=benzyl and $R^2$=tetrahydropyranyl in formula III').

The powder thus obtained was dissolved in 50 ml of methanol, to which were then added 0.4 ml of triethylamine and 1.35 g (5.7 mmol) of tert-butyl 4,6-dimethylpyrimidyl-2-thiolcarbonate. After stirring the mixture at ambient temperature overnight, the resultant reaction solution was evaporated under reduced pressure to leave a residue, which was taken up in 20 ml of toluene, followed by addition of n-hexane to separate a precipitate. The precipitate was collected by filtration and washed with water to afford 2.24 g of a powder of 3,2',6'-tri-N-benzyloxycarbonyl-1-N-tert-butoxycarbonyl-3',4'-dideoxy-5-O-tetrahydropyranylneamine.

A solution of this powder dissolved in 50 ml of pyridine was admixed with 574 mg (5.7 mmol) of methanesulfonyl chloride, and the mixture was agitated overnight at ambient temperature. The resulting reaction solution was concentrated to dryness and the residue was purified by column chromatography on silica gel (150 g of Wako-gel C-200) developed with toluene-acetone (5:1) to yield 1.65 g (60%) of the titled compound. Decomposition point 101°–105° C. $[\alpha]_D^{22}$ +29° (c 0.44, $CHCl_3$).

(e) Preparation of
3-O-benzyol-1,2',6'-tri-N-benzyloxycarbonyl-4-N-tert-butoxycarbonyl-5-O-tetrahydropyranyl-$N^4$-deglycyl-tri-$N^4$,$N^{6'}$,$O^3$-demethylistamycin A ($R^1$=benzyl, $R^2$=tetrahydropyranyl, $R^3$=tert-butyl and $R^5$=benzoyl in formula VI)

1.37 g (1.43 mmol) of the product from step (d) above was dissolved in 55 ml of dry tetrahydrofuran, and to the solution was added 194 mg (3.6 mmol) of sodium methylate at 0° C. under an atmosphere of argon gas. The mixture obtained was stirred for 30 minutes and then left to stand at 10° C. for 15 hours. The resultant reaction solution was admixed with an excessive amount of ammonium chloride and water, followed by extraction with chloroform. The extract was concentrated to dryness to give 1.23 g of a powder of the aziridine derivative ($R^1$=benzyl, $R^2$=tetrahydropyranyl and $R^3$=tert-butyl in formula V). $[\alpha]_D^{22}$ +10° (c 0.5, $CHCl_3$). $R_f$ 0.41 in silica gel TLC developed with benzene-ethyl acetate (1:1).

1.12 g of the powder so obtained was dissolved in 50 ml of dimethylformamide, to which was then added 1.3 g of sodium benzoate and the mixture was allowed to stand at room temperature for 10 hours to effect the fission of the aziridine ring. The resultant reaction solution was admixed with 300 ml of chloroform and washed twice with saturated aqueous sodium chloride. The chloroform layer was separated, dried over anhydrous sodium sulfate and concentrated to dryness. The residue was purified by column chromatography on silica gel (180 g of Wako-gel C-200) developed with toluene-ethyl acetate (5:2) to yield 878 mg (76%) of the title compound. Decomposition point 84°–86° C. $[\alpha]_D^{22}$ +61° (c 0.49, $CHCl_3$). $R_f$ 0.54 in silica gel TLC developed with benzene-ethyl acetate (1:1).

(f) Preparation of tri-$N^1,N^{2'},N^{6'}$-benzyloxycarbonyl-$N^4$-tert-butoxycarbonyl-$O^5$-tetrahydropyranyl-$N^4$-deglycyltri-$N^4,N^{6'},O^3$-demethylistamycin A ($R^1$=benzyl, $R^2$=tetrahydropyranyl, $R^3$=tert-butyl and $R^5$=H in formula IV)

860 mg (0.88 mmol) of the product obtained in step (e) was dissolved in 20 ml of a mixture of 12% methanolic ammonia and the solution was allowed to stand at ambient temperature for 40 hours to effect removal of 3-O-benzoyl group. The resultant reaction solution was concentrated to dryness and the residue was chromatographed on silica gel (70 g of Wako-gel C 200) using benzene-ethyl acetate (1:1) as the developing solvent to give 693 mg (90%) of the title compound. Decomposition point 88°–90° C. $[\alpha]_D^{22}$ +44° (c 0.5, CHCl$_3$). $R_f$ 0.18 in silica gel TLC developed with benzene-ethyl acetate (1:1).

(g) Preparation of
$N^4$-deglycyl-di-$N^{6'},O^3$-demethylistamycin A
(compound of formula VIII)

680 mg (0.78 mmol) of the product from step (f) above was dissolved in 10 ml of 90% aqueous trifluoroacetic acid at 0° C. and kept aside for two hours to effect hydrolytic removal of the tetrahydropyranyl group with eventual removal of the tert-butoxycarbonyl group. The reaction solution was then concentrated to dryness. The residue obtained was taken up in 50 ml of chloroform and washed successively with 1N aqueous sodium hydroxide and water. The chloroform layer was separated, dried over anhydrous sodium sulfate and concentrated to dryness. The residue was purified by column chromatography on silica gel (50 g of Wako-gel C 200) developed with a mixed solvent of chloroform-methanol-17% aqueous ammonia (80:10:1) to afford 350 mg (65%) of a powder of $N^1,N^{2'},N^{6'}$-benzyloxycarbonyl-$N^4$-deglycyl-tri-$N^4,N^{6'},O^3$-demethylistamycin A.

To a solution of 293 mg (0.42 mmol) of the powder obtained just above in 5 ml of methanol was added a solution of 27 mg of sodium carbonate in 0.5 ml of water, followed by addition of 55 mg (0.5 mmol) of ethyl chloroformate at 0° C. The resulting mixture was stirred at room temperature for two hours to effect introduction of ethoxycarbonyl group, after which the reaction solution was concentrated to dryness after the residue was taken up in 30 ml of chloroform and washed with water. The chloroform layer was then dried over anhydrous sodium sulfate and again concentrated to dryness to give 318 mg (98%) of a powder of tri-$N^1,N^{2'},N^{6'}$-benzyloxycarbonyl-$N^4$-ethoxycarbonyl-$N^4$-deglycyl-tri-$N^4,N^{6'},O^3$-demethylistamycin A ($R^1$=benzyl and $R^3$=ethyl in formula VII). $R_f$ 0.62 in silica gel TLC developed with a mixed solvent of chloroform-methanol-17% aqueous ammonia (80:10:1).

The powder thus obtained was dissolved in 8 ml of a mixture of methanol, water and acetic acid (2:1:1), to which was then added 100 mg of 5% palladium-carbon as hydrogenolysis catalyst and the mixture was allowed to stand under a stream of hydrogen gas for two hours to effect the removal of benzyloxycarbonyl groups. Thereafter, the catalyst was removed from the reaction mixture, which was then concentrated to dryness. A solution of the residue dissolved in water was passed through a column of 11 ml of Amberlite CG-50 (NH$_4$ form, a product of Rohm & Haas Co., USA). The column was washed successively with water and 0.1M aqueous ammonia and then eluted with 0.2M aqueous ammonia. The eluate from the column was concentrated to dryness to give 143 mg (95%) of a powder of $N^4$-ethoxycarbonyl-$N^4$-deglycyl-tri-$N^4,N^{6'},O^3$-demethylistamycin A ($R^3$=ethyl in formula VII'). $R_f$ 0.55 in silica gel TLC developed with chloroform-methanol-17% aqueous ammonia (3:3:1).

130 mg (0.36 mmol) of the powder prepared just above was dissolved in 6 ml of anhydrous trifluoroacetic acid at 0° C., the solution was concentrated to dryness and the residue was taken up in 3 ml of dry tetrahydrofuran. To the resultant solution was added 15 ml of 1M boron hydridetetrahydrofuran complex (a product of Aldorich Co., U.S.) and the mixture was agitated at 50° C. for 18 hours to effect the reductive conversion of the ethoxycarbonylamino group into the methylamino group. An amount of water was added to the reaction solution, which was then concentrated to dryness and the residue was taken up in 10 ml of water. The aqueous solution was adjusted to pH 8 by addition of aqueous ammonia and passed through a column of 30 ml of Amberlite CG-50 (NH$_4$ form). The column was washed successively with water and 0.2M, 0.3M and 0.4M aqueous ammonia solutions and then eluted with 0.5M aqueous ammonia. The eluate was collected and concentrated to dryness to yield 45 mg (40%) of monocarbonate of the title compound in the powder form. Decomposition point 115°–118° C. $[\alpha]_D^{22}$ +102° (c 0.65, H$_2$O). Mass spectrometry: m/e 304 (M+). TLC on silica gel: $R_f$ 0.12 when developed with the lower layer of chloroform-methanol-28% aqueous ammonia (2:1:1) and $R_f$ 0.50 when developed with butanol-ethanol-chloroform-17% aqueous ammonia (4:5:2:5).

EXAMPLE 2

Preparation of di-$N^{6'},O^3$-demethylistamycin A (final compound of formula I)

45 mg (0.123 mmol) of $N^4$-deglycyl-di-$N^{6'},O^3$-demethylistamycin A monocarbonate obtained in step (g) of Example 1 above was dissolved in 3 ml of methanol, and to the solution were added 0.017 ml (0.123 mmol) of triethylamine and 94.9 mg (0.38 mmol) of N-benzyloxycarbonyloxysuccinimide

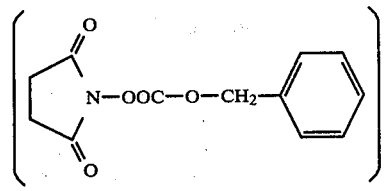

The resultant mixture was allowed to stand at room temperature for 6.5 hours to effect the introduction of the benzyloxycarbonyl groups as an amino-protecting group. The reaction solution comprising tri-$N^1,N^{2'},N^{6'}$-benzyloxycarbonyl-$N^4$-deglycyl-di-$N^{6'},O^3$-demethylistamycin A so produced was then concentrated to dryness and the residue was taken up in 3 ml of dioxane, followed by addition of 67.9 mg (0.18 mmol) of N-hydroxysuccinimide ester of N-benzyloxycarbonylglycine. The mixture thus obtained was kept aside at 60° C. for 6 hours to perform the introduction of the glycyl group, after which the reaction solution comprising tetra-$N^1,N^{2'},N^{6'},N^{2''}$-benzyloxycarbonyl-di-$N^{6'},O^3$-demethylistamycin A as formed was concentrated to dryness and the residue was dissolved in 4 ml of a mixed solvent of acetic acid, methanol and water (2:1:1).

To the resulting solution was added 50 mg of 5% palladium-carbon as a hydrogenolysis catalyst and the mixture was allowed to stand under a stream of hydrogen gas for 4 hours to effect the deprotection reaction for removal of the benzyloxycarbonyl groups. The reaction mixture was filtered to remove the catalyst, the filtrate was concentrated to dryness and the residue was taken up in water. The aqueous solution obtained was passed through a column of 6 ml of Amberlite CG-50 (NH4 form) and the column was washed successively with water, 0.1M aqueous ammonia and 0.3M aqueous ammonia and then eluted with 0.4M aqueous ammonia. The eluate was collected in 1 ml-fractions, and the active fraction Nos. 4–10 were combined together and concentrated to dryness to yield 15 mg (29%) of di-$N^{6'},O^3$-demethylistamycin A monocarbonate in the powder form. m.p. 138°–145° C. (decomp.), $[\alpha]_D^{22}$ +136° (c 0.36, water).

What we claim is:

1. A process for preparing di-$N^{6'}$, $O^3$-demethylistamycin A of the formula (I), which comprises the consecutive steps of:

(a) protecting the four amino groups of 3',4'-dideoxyneamine of the formula (II)

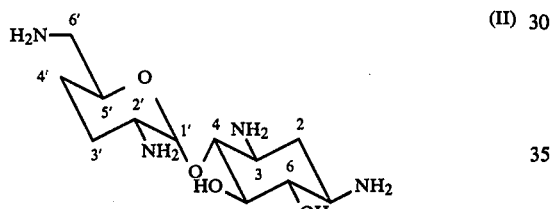

with an amino-protecting group of the formula

where $R^1$ is an alkyl group of 1–4 carbon atoms, a cycloalkyl group of 5–6 carbon atoms or a benzyl group, to produce a tetra-N-protected 3',4'-dideoxyneamine of the formula (II')

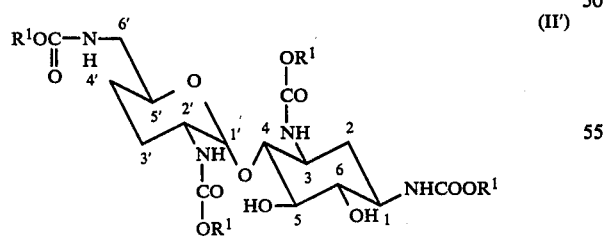

wherein each $R^1OCO$— stands for the monovalent amino-protecting group of urethane-forming type where $R^1$ is as defined above, (b) converting this tetra-N-protected 3',4'-dideoxyneamine (II') into its 1,6-cyclic carbamate derivative by reacting with an alkali metal hydride, to produce said 1,6-cyclic carbamate derivative of the formula (II''):

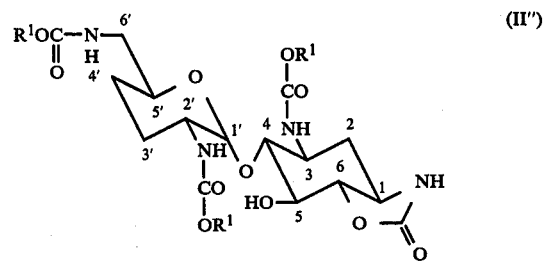

wherein $R^1$ is as defined above, (c) protecting the 5-hydroxyl group of said 1,6-carbamate derivative (II'') with a hydroxyl-protecting group ($R^2$) which is selected from an alkyl group of 1–4 carbon atoms, benzyl group and tetrahydropyranyl group, to produce a compound of the formula (III)

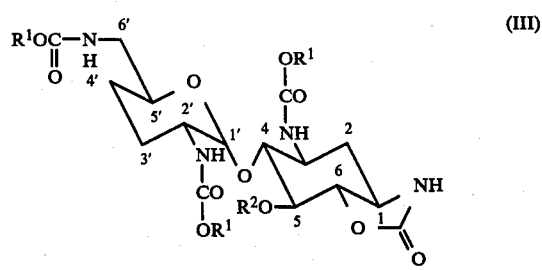

wherein $R^1$ and $R^2$ are as defined above, (d) treating the compound (III) with aqueous sodium or barium hydroxide to hydrolyze its 1,6-cyclic carbamate ring and thereby to produce the compound of the formula (III')

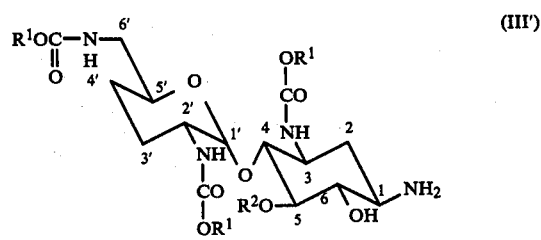

wherein $R^1$ and $R^2$ are as defined above, (e) protecting the liberated 1-amino group of the compound (III') with an amino-protecting group —$COR^3$ where $R^3$ is an alkyl group of 1–4 carbon atoms, a cycloalkyl group of 5–6 carbon atoms or a benzyl group but must be different from the $R^1$ present in the already existing amino-protecting groups

to produce the compound of the compound of the formula (III'')

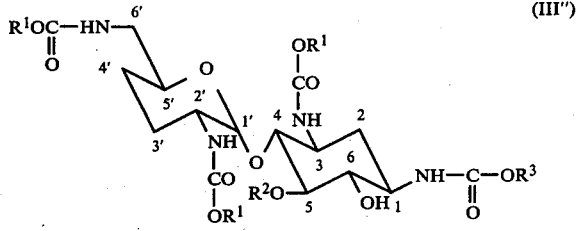
(III″)

wherein $R^1$, $R^2$ and $R^3$ are as defined above,
(f) sulfonylating the 6-hydroxyl group of the compound (III″) with a sulfonylation reagent of the formula $R^4SO_3H$ where $R^4$ is an alkyl group of 1–4 carbon atoms, an aryl group of 5–6 carbon atoms or a benzyl group, to produce a compound of the formula (IV)

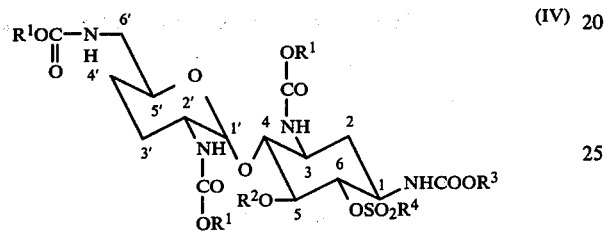
(IV)

wherein $R^1$, $R^2$, $R^3$ and $R^4$ are as defined above,
(g) reacting the compound (IV) with an alkali metal alcoholate to form a compound bearing an aziridine ring and having the formula (V):

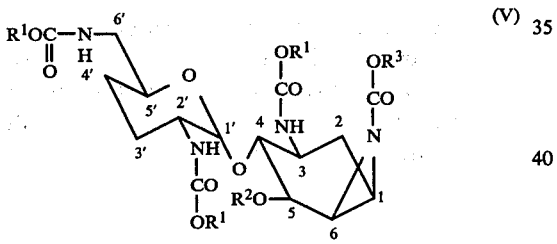
(V)

wherein $R^1$, $R^2$ and $R^3$ are as defined above,
(h) reacting the compound (V) with an alkali metal salt of a lower alkanoic acid or benzoic acid to open the aziridine ring of the compound (V) and thereby to produce a compound of the formula (VI):

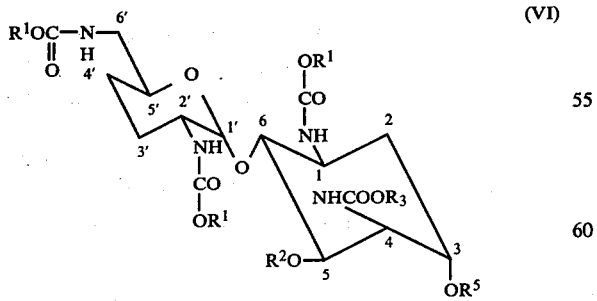
(VI)

wherein $R^1$, $R^2$ and $R^3$ are as defined above and $R^5$ represents an acyl group which originates from the alkanoic or benzoic acid employed,
(i) removing the two hydroxyl-protecting groups ($R^2$ and $R^5$) from the 3- and 5-positions of the compound (VI) to produce a compound of the formula (VII)

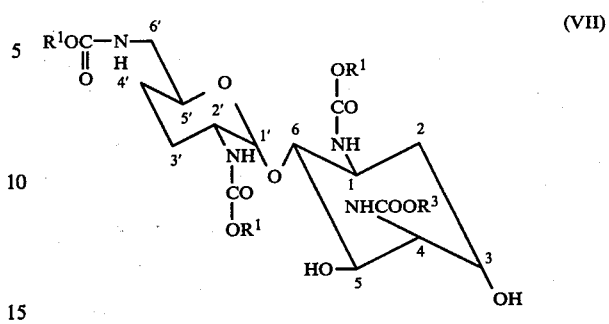
(VII)

wherein $R^1$ and $R^3$ are as defined above,
(j) removing preferentially the amino-protecting groups (—COOR$^1$) from the 1-, 2′- and 6′-positions of the compound (VII), and thereby to produce a compound of the formula (VII′)

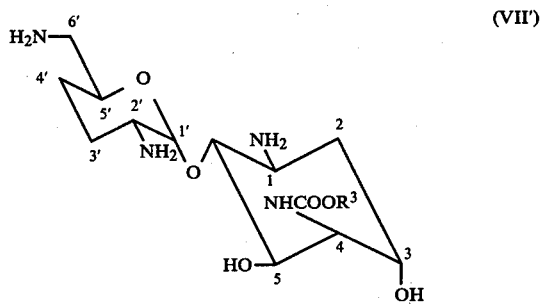
(VII′)

wherein $R^3$ is as defined above,
(k) reducing the group (—NHCOOR$^3$) of the compound (VII′) with a metal hydride into the 4-methylamino group and thereby to produce the compound, $N^4$-deglycyl-di-$N^{6'}$, $O^3$-demethylistamycin A of the formula (VIII)

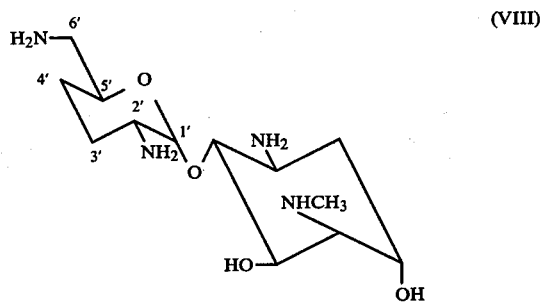
(VIII)

(1) protecting the three 1-, 2′- and 6′-amino groups of the compound (VIII) with a known amino-protecting groups to produce a 1,2′,6′-tri-N-protected derivative of the compound (VIII),
(m) reacting said 1,2′,6′-tri-N-protected derivative with glycine or an N-protected glycine derivative to acylate (glycylate) the 4- methylamino group of said 1,2′,6′-tri-N-protected derivative and thereby to produce the 1,2′,6′-tri-N-protected derivative of di-$N^{6'}$,$O^3$-demethylistamycin A, and
(n) removing all the remaining amino-protecting groups from said 1,2′,6′-tri-N-protected derivative of di-$N^{6'}$,$O^3$-demethylistamycin A to afford the desired di-$N^{6'}$,$O^3$-demethylistamycin A.

* * * * *

UNITED STATES PATENT AND TRADEMARK OFFICE
CERTIFICATE OF CORRECTION

PATENT NO. : 4,474,946

DATED : Oct. 2, 1984

INVENTOR(S) : UMEZAWA et al

It is certified that error appears in the above-identified patent and that said Letters Patent is hereby corrected as shown below:

On the cover page of the patent, left hand side, under Related U.S. Application Data, delete "Pat. No. 4,379,687" and substitute therefor --Abandoned--.

Signed and Sealed this

Eleventh Day of June 1985

[SEAL]

Attest:

DONALD J. QUIGG

Attesting Officer

Acting Commissioner of Patents and Trademarks